US008365733B2

(12) United States Patent
Rutan

(10) Patent No.: US 8,365,733 B2
(45) Date of Patent: Feb. 5, 2013

(54) LINER FOR USE WITH RESPIRATORY MASK

(76) Inventor: Robert M. Rutan, Jackson, MI (US)

( * ) Notice: Subject to any disclaimer, the term of this patent is extended or adjusted under 35 U.S.C. 154(b) by 700 days.

(21) Appl. No.: 12/469,998

(22) Filed: May 21, 2009

(65) Prior Publication Data

US 2009/0293880 A1   Dec. 3, 2009

Related U.S. Application Data

(60) Provisional application No. 61/056,893, filed on May 29, 2008.

(51) Int. Cl.
  *A62B 18/08* (2006.01)
(52) U.S. Cl. .......... 128/206.24; 128/206.21; 128/207.11
(58) Field of Classification Search ............. 128/206.21, 128/206.23–206.26, 206.28, 207.11
  See application file for complete search history.

(56) References Cited

U.S. PATENT DOCUMENTS

| | | | | |
|---|---|---|---|---|
| 3,357,426 | A | * | 12/1967 | Cohen .................. 128/202.27 |
| 5,243,971 | A | | 9/1993 | Sullivan et al. |
| 6,196,223 | B1 | * | 3/2001 | Belfer et al. ............ 128/206.25 |
| 6,338,340 | B1 | | 1/2002 | Finch et al. |
| 6,698,427 | B1 | | 3/2004 | Clowers |
| 6,926,004 | B2 | * | 8/2005 | Schumacher ............ 128/206.27 |
| 7,234,466 | B2 | | 6/2007 | Kwok et al. |
| 7,472,703 | B2 | | 1/2009 | Hernandez et al. |
| 2003/0023182 | A1 | | 1/2003 | Mault et al. |
| 2004/0244804 | A1 | | 12/2004 | Olsen et al. |
| 2005/0199239 | A1 | | 9/2005 | Lang et al. |
| 2005/0279367 | A1 | | 12/2005 | Klemperer |
| 2006/0060200 | A1 | | 3/2006 | Ho et al. |
| 2006/0130845 | A1 | | 6/2006 | Schegerin |
| 2007/0017525 | A1 | | 1/2007 | Madaus et al. |
| 2007/0157934 | A1 | | 7/2007 | Lang et al. |
| 2007/0175479 | A1 | | 8/2007 | Groll |
| 2009/0107507 | A1 | | 4/2009 | Moore |
| 2009/0139525 | A1 | | 6/2009 | Schirm |

OTHER PUBLICATIONS

International Preliminary Report on Patentability and Written Opinion for PCT/US2009/045256 dated Dec. 9, 2010.
International Search Report for the corresponding International Application No. PCT/US2009/045256 mailed Jul. 20, 2009.
www.cpaptalk.com, May 6, 2005-Nov. 30, 2005.

* cited by examiner

*Primary Examiner* — Lynne Anderson
(74) *Attorney, Agent, or Firm* — Brooks Kushman P.C.

(57) ABSTRACT

A liner for use with a respiratory mask having a face-engaging portion, such as a CPAP mask, includes a body constructed from an absorbent material, the body having an outer edge, an inner edge, and an opening bounded by the inner edge. A perimeter of the outer edge is larger than a perimeter of the face-engaging portion of the respiratory mask for forming an extending portion of the body, and the liner is configured to be releasably held by the mask and a user's face such that the outer edge extends beyond the face-engaging portion.

20 Claims, 5 Drawing Sheets

LINER FOR USE WITH RESPIRATORY MASK

CROSS-REFERENCE TO RELATED APPLICATIONS

This application claims the benefit of U.S. provisional application Ser. No. 61/056,893 filed May 29, 2008, which is incorporated by reference herein.

BACKGROUND OF THE INVENTION

1. Field of the Invention

This invention relates to a liner for use with a respiratory mask, such as a CPAP mask.

2. Background Art

Obstructive sleep apnea is a serious and potentially fatal medical condition in which a person's airway becomes physically blocked multiple times during sleep, restricting oxygen intake and causing the person to awake gasping for breath. Possible effects of the condition include extreme fatigue, high blood pressure, strokes, heart attacks, and sometimes even death.

One of the most common treatments of obstructive sleep apnea is the use of a continuous positive airway pressure (CPAP) machine. These machines deliver a continuous flow of pressurized air to the airway through a hose and mask fitted to the face. Patient compliance is a major problem with CPAP users, however, due to discomfort, air leaks, and general ineffectiveness. It is estimated that up to 50% of users discontinue use.

Most CPAP masks currently available are made from silicone, rubber, vinyl, or a nylon-based fabric. These materials are typically water and gas impermeable, which can block off pores, cause sweating, and create pressure marks on the face, increasing the discomfort of the mask. Furthermore, most mask manufacturers recommend against the use of skin or face cream with CPAP masks such the mask material directly contacts the skin. This is a problem for many users, especially those that have dry skin and depend on night cream for skin care.

DETAILED DESCRIPTION OF THE INVENTION

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

One or more embodiments of the present invention provide an accessory capable of improving the comfort, effectiveness, and/or patient compliance of CPAP and other respiratory masks.

Figure 1:
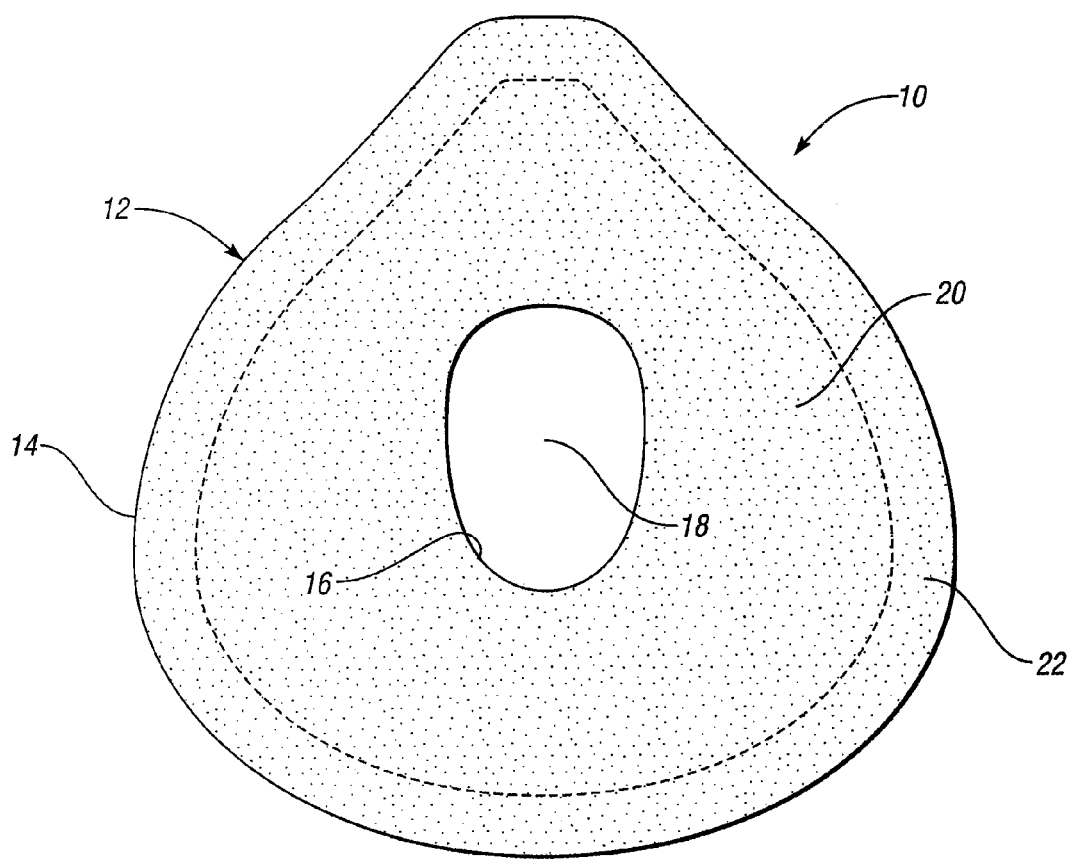
FIG. 1 is a top plan view of a liner according to an aspect of the present invention, such as for use with a full-face respiratory mask.
Figure 2:
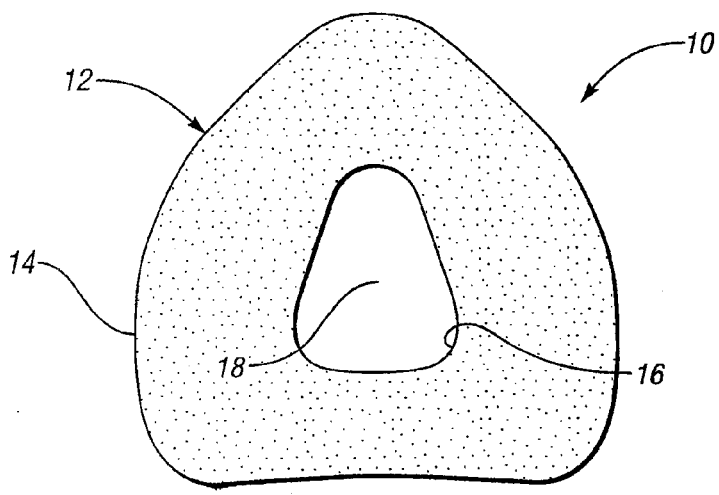
FIG. 2 is a top plan view of a liner according to an aspect of the present invention, such as for use with a nasal respiratory mask.
Figure 3:
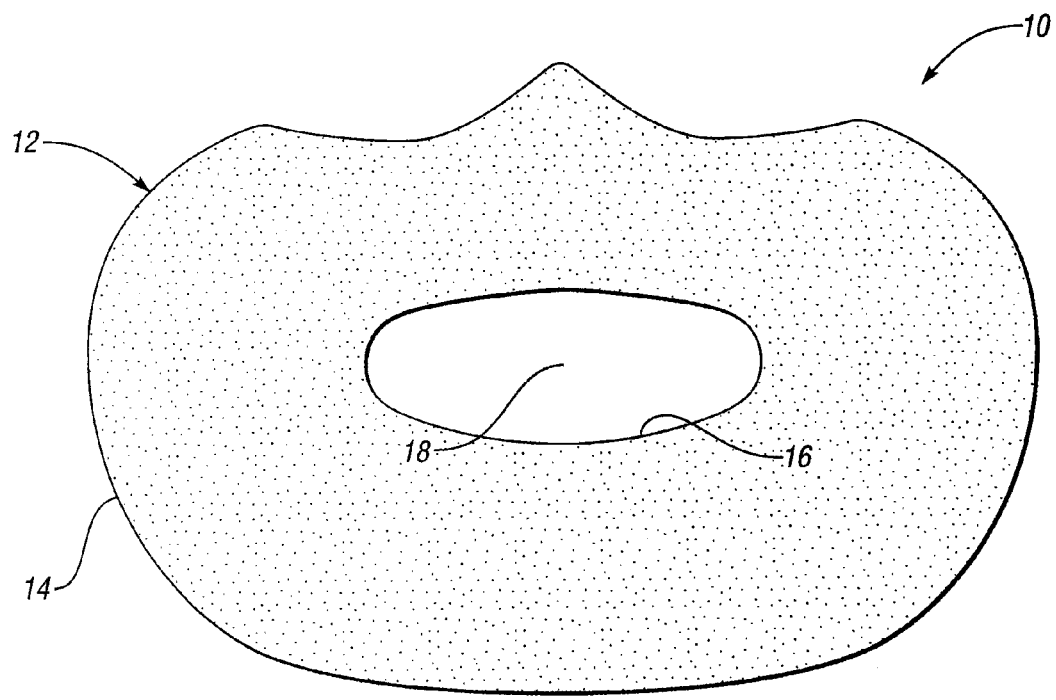
FIG. 3 is a top plan view of a liner according to an aspect of the present invention, such as for use with a partial-face respiratory mask.

With reference to FIGS. 1-3, a liner for use with a respiratory mask, such as a CPAP mask M (see FIG. 5), is illustrated and designated generally by reference numeral 10. In use, the liner 10 according to an aspect of the present invention is positioned between and held in place by the respiratory mask and the face of a user in order to absorb moisture, maintain proper positioning of the mask M, and greatly reduce or eliminate air from leaking between the mask M and the user's face. Although the liner 10 is described herein primarily in relation to use with a CPAP mask, it is understood that the liner 10 may also be used with other types of respiratory masks such as, but not limited to, oxygen masks, respirators, and filtering masks.

According to an aspect of the present invention, the liner 10 includes a body 12 having an outer edge 14, an inner edge 16, and an opening 18 bounded by the inner edge 16. The body 12 may be generally oval-shaped, elliptical, round, or triangular, or have any other shape appropriate for use with a respiratory mask, and is not limited to those shapes depicted herein. The opening 18 is configured to at least partially receive the nose, mouth, or both nose and mouth, depending upon the type of mask, allowing air flow from an air source to be received by the user through the mask M. The opening 18 may be generally elliptical or oval-shaped as shown, but is not intended to be limited to these shapes.

Figure 5:
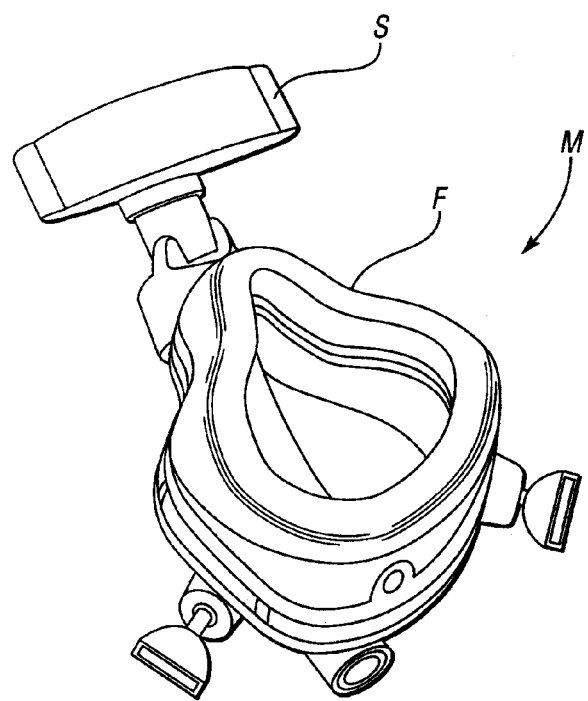
FIG. 5 is a perspective view of an exemplary full-face respiratory mask.

Referring to FIGS. 1 and 5, the outer edge 14 of liner 10 may have a shape scaled to a general shape of a face-engaging portion F of the respiratory mask M. As best shown in FIGS. 6-10, a perimeter of the liner outer edge 14, which may be continuous or discontinuous, is larger than a perimeter of the face-engaging portion F, wherein the liner 10 is configured to be releasably held between the mask M and a user's face such that the outer edge 14 extends beyond the mask face-engaging portion F around at least part of its perimeter. As such, as illustrated in an exemplary manner in FIG. 1, the body 12 has a first portion 20 inward of the perimeter of the face-engaging portion F and a second, extending portion 22 outward of the perimeter of the face-engaging portion F. The extending portion 22 extends outwardly from the face-engaging portion F, and may generally follow the contours of the user's face. Thus, when the liner 10 is releasably held by the mask M and the user's face, the outer edge 14 is spaced apart from the mask M.

In one embodiment, the outer edge 14 may extend beyond the perimeter of the mask face-engaging portion F by between about 0.25 to 1.0 inches, or more particularly may extend between about 0.5 and 0.75 inches. In general, the area of the extending portion 22 may comprises at least about 5%, 10%, or 15% of the area of the body 12, but larger proportions of area represented by the extending portion 22 are also contemplated in accordance with an aspect of the present invention. By allowing the outer edge 14 of the liner 10 to loosely protrude beyond the mask M, the extending portion 22 serves to reduce air leaks from the perimeter of the mask M by acting as a baffle to regulate, limit, or diffuse air flow between the mask M and the skin, thus also stopping any resulting squealing-type noises created by such air leaks.

According to an aspect of the present invention, the body 12 is constructed from a single layer of absorbent material, wherein the thickness of the body 12 may be between about 0.005 to 0.05 inches, although these dimensions are not intended to be limiting. In one embodiment, the material may include cotton. In another embodiment, the material may include another material, such as silicone, with cotton embedded therein. However, it is understood that any material with suitable absorption and comfort properties may be used. In further accordance with an aspect of the present invention, the material used for the construction of the body 12 may be stretchable to aid in adjusting and customizing the fit of the liner 10 to a particular user as described below. The absorbent material may function to absorb moisture and/or oils from the user's skin and enable the mask M to maintain a consistent and comfortable position with respect to the user's face when in use.

In a CPAP system, an air source (not shown) delivers a constant flow of pressurized and humidified air to the CPAP mask M. Due to the moisture of the humidified air, facial perspiration (such as due to contact with the mask material), and oil from the skin, the mask M may slip on the user's face, thus leaking air and awakening the user during sleep. The liner 10 according to an aspect of the present invention may absorb such moisture and wick it away from the face and mask surfaces. As a result, proper positioning of the mask M with respect to the skin may be maintained, thus eliminating or greatly reducing air leaks and facilitating the ability for a user to wear their CPAP mask successfully throughout the night.

The single layer construction of the liner 10 may act as a sort of "second skin" upon the user's face. As such, the liner 10 is able to provide its baffle function without detracting from the prescribed fit of the mask M since the liner 10 does not appreciably alter the distance of the face-engaging portion F from the user's face. Pressure markings from the mask M may also be reduced or eliminated by use of the liner 10 according to an aspect of the present invention. Furthermore, the absorbent liner material may make use of facial creams possible while wearing the mask M, since direct contact of the skin with the mask material is avoided.

According to an aspect of the present invention, the liner 10 is held in place by the pressure of the respiratory mask M upon the face (e.g., by straps around the head). While it is contemplated that the liner 10 could be at least partially fastened to the mask M, advantageously neither elastic nor another mechanism for securing the liner 10 to the mask M is required, allowing for ease of use and manufacture. The position of the liner 10 can be adjusted if necessary while the mask M is secured, and the liner 10 is easily removable and replaceable when the mask M is removed.

Respiratory masks, more particularly CPAP masks, are offered in various shapes and sizes, including full-face, nasal, and partial-face (hybrid) configurations. Full-face masks typically include a wider bottom region for covering the mouth area and a narrower upper region for covering the nasal area. Nasal masks generally cover the nasal area and not the mouth area. Partial-face (hybrid) masks generally cover the mouth and may include a nasal interface. It is therefore contemplated that the outer edge 14 of liner 10 may have a shape similar to a general shape of the face-engaging portion F for a selected mask M, wherein the shape of the outer edge 14 may represent a scaled version of the general shape of the face-engaging portion F.

If the liner 10 is to be used with a full-face CPAP mask, the opening 18 may be sized to at least partially receive the user's nose and mouth (see FIG. 1). In this embodiment, the opening 18 may have a length of between about 1.0 to 3.0 inches and a width of between about 1.0 to 1.75 inches, and the body 12 may have a length of between about 4.5 to 7.5 inches and a width of between about 4.5 to 6.5 inches. If the liner 10 is to be used with a nasal CPAP mask, the opening 18 may be sized to at least partially receive the user's nose (see FIG. 2). In this embodiment, the opening 18 may have a length of between about 1.25 to 1.75 inches and a width of between about 0.75 to 1.5 inches, and the body 12 may have a length of between about 3.0 to 4.0 inches and a width of between about 3.0 to 5.0 inches. If the liner 10 is to be used with a partial-face CPAP mask, the opening 18 may be sized to at least partially receive the user's mouth (see FIG. 3). In this embodiment, the opening 18 may have a length of between about 0.5 and 1.0 inches and a width of between about 1.75 and 2.25 inches, and the body 12 may have a length of between about 2.5 to 4.0 inches and a width of between about 4.25 and 6.0 inches. It is understood, however, that these embodiments are not intended to be limiting, and the liner 10 could be configured to fit any size or shape of CPAP mask M.

Figure 4:
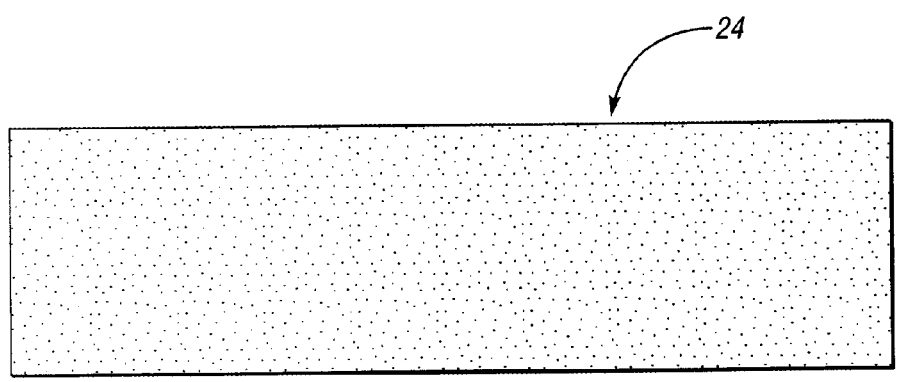
FIG. 4 is a top plan view of a forehead liner according to an aspect of the present invention.

Turning to FIG. 4, a forehead liner 24 may also be provided to interface with a forehead stabilizer portion S of a respiratory mask M (see FIG. 5) to create a two-piece liner system in accordance with an aspect of the present invention. The forehead liner 24 is configured to be releasably held by the forehead stabilizer portion S and the user's face, and may have an area at least as large as an area of the forehead stabilizer portion S. The forehead liner 24 may have a generally rectangular shape, and may comprise a single or multi-layer material such as, but not limited to, cotton. In one embodiment, the forehead liner 24 comprises three layers of an absorbent material. The forehead liner 24 may have a shape that is generally similar to the shape of the forehead stabilizer portion S, and may extend beyond the perimeter of the forehead stabilizer portion S by between about 0.5 to 0.75 inches, although it is understood that the forehead liner 24 is not limited to this configuration. Liner 10 and forehead liner 24 may be used together, but may also be used separately as desired by a user.

Figure 6:
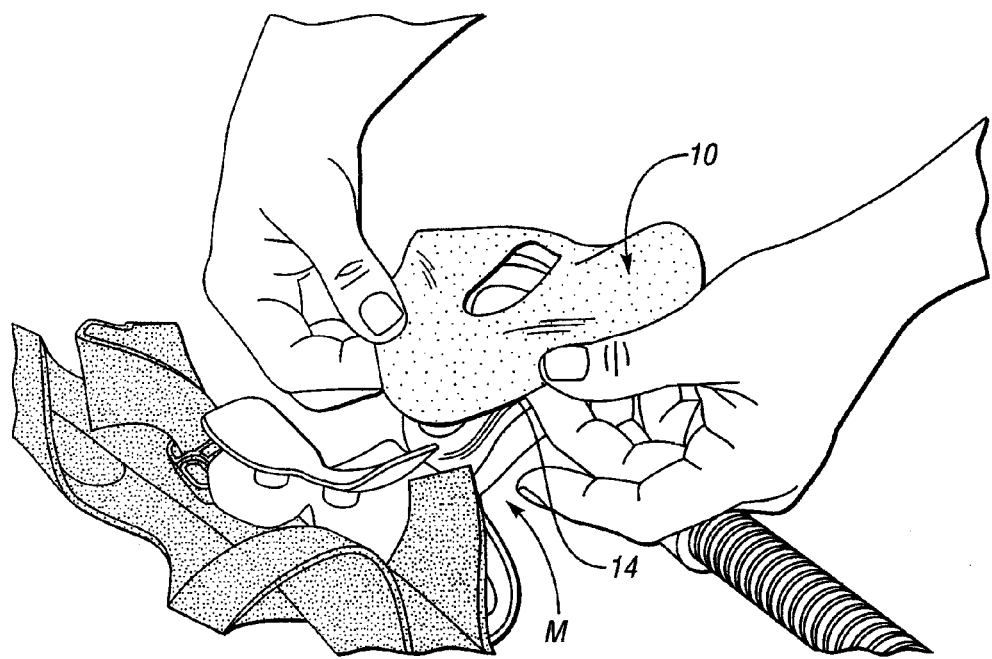
FIG. 6 is a photograph illustrating placement of a liner in accordance with an aspect of the present invention on the face-engaging portion of a respiratory mask.
Figure 7:
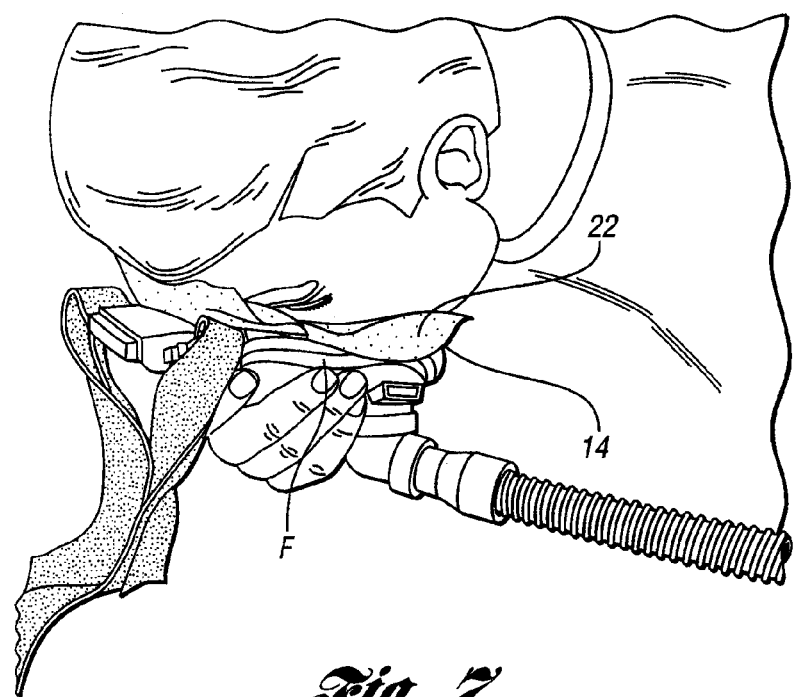
FIG. 7 is a photograph illustrating a user engaging the liner placed on the mask, fitting her nose and mouth into the liner opening.
Figure 8:
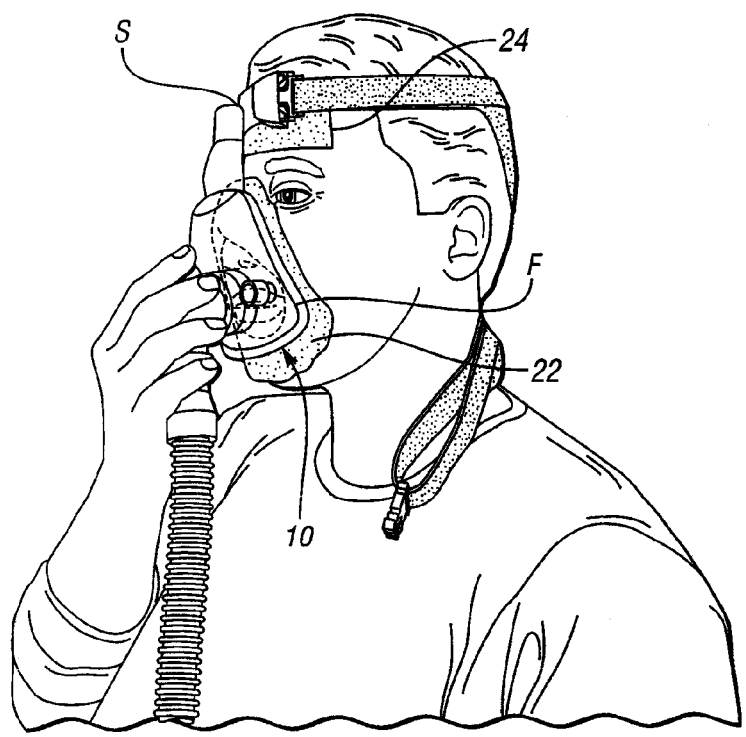
FIG. 8 is a photograph illustrating a user returning her head to an upright position while holding the mask and liner against her face.
Figure 9:
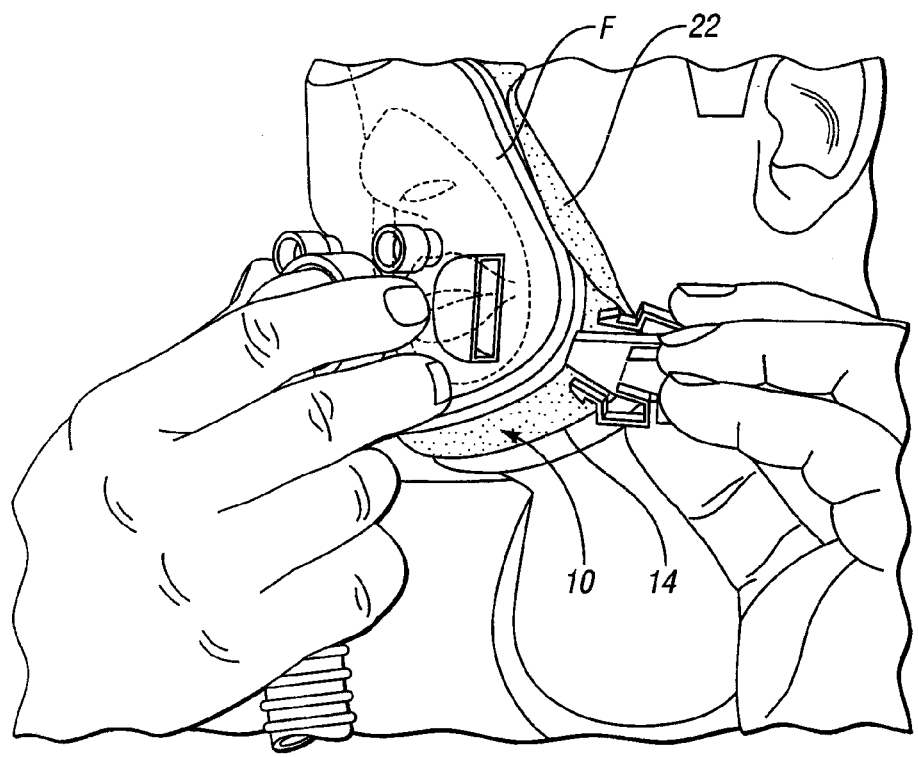
FIG. 9 is a photograph illustrating a user attaching the mask straps.
Figure 10:
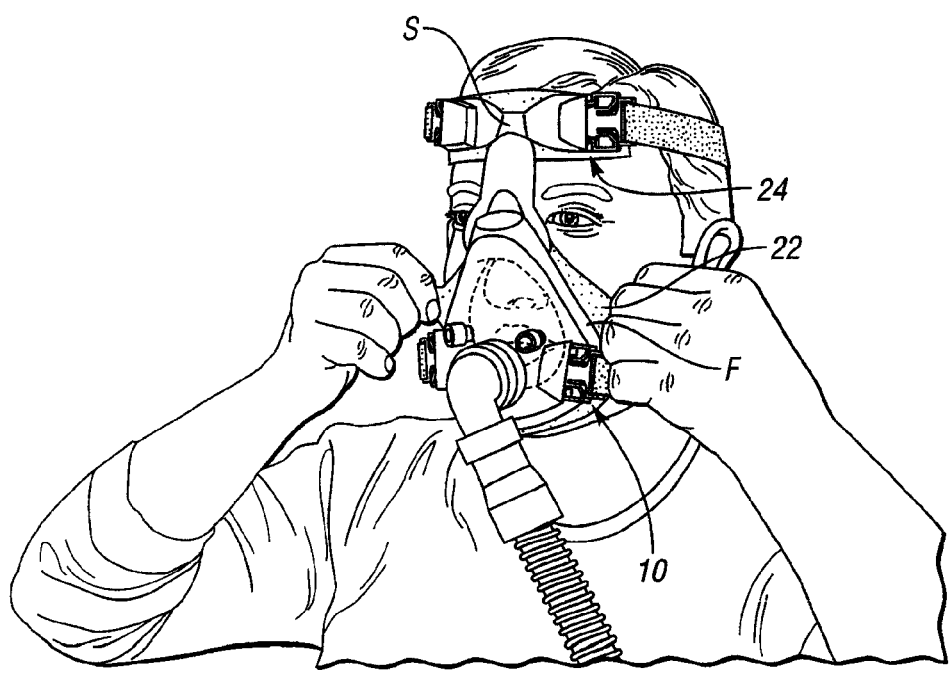
FIG. 10 is a photograph illustrating a user adjusting the positioning of the liner by pulling on the second portion of the liner body protruding beyond the perimeter of the face-engaging portion.

Referring now to FIGS. 6-10, a method of using the liner 10 according to an aspect of the present invention will be described. As shown in FIG. 6, the liner 10 may be placed over the face-engaging portion F such that the outer edge 14 extends beyond and is spaced apart the face-engaging portion F. Although not shown in this figure, the forehead liner 24 can also be placed on the forehead stabilizer portion S if desired. The user may then lean his/her face downward toward the mask M, fitting his/her nose and/or mouth (as applicable) into the opening 18 as depicted in FIG. 7. Next, the user may press his/her face against the liner 10 and mask M while returning his/her head to a normal upright position as shown in FIG. 8. As illustrated in FIG. 9, the user may then snap the mask fasteners into place and adjust their tightness to secure the mask M. Securing the mask M releasably holds the liner 10 between the face-engaging portion F and a user's face, such that the liner 10 regulates air flow and reduces air leaks between the face-engaging portion F and the user's face. Lastly, with reference to FIG. 10, the liner 10 may be adjusted, such as around the nose and mouth, by pulling outward on the protruding extending portion 22, thereby providing a customized fit for a particular user. Of course, it is understood that variations on the above-described use of liner 10 and forehead liner 24 are fully contemplated in accordance with the present invention.

After a night of use, the liner 10 and forehead liner 24 may be reused or may be discarded and replaced with another liner 10, 24. Since the liners 10, 24 are absorbent, it may be advantageous to replace them periodically should they become dirty, saturated, or otherwise unsatisfactory. In one embodiment, liner 10 may be replaced about every 1 to 2 days, and forehead liner 24 may be used for up to 7 days and then replaced, although these time periods are not intended to be limiting. Advantageously, use of liner 10 and/or liner 24 prevents direct skin contact with the mask material, decreasing the need to clean the mask M as frequently.

CPAP therapy is the most widely used method for treating sleep apnea, but it is only successful when the equipment fits and works properly and allows the user to stay asleep and experience deep-sleep, rapid eye movement (REM) cycles, the sleep cycle in which the most beneficial rest takes place. According to an aspect of the present invention, the liner 10 may facilitate a more comfortable and effective CPAP therapy by contributing to a good fit of the CPAP mask M, providing comfort to the user, and reducing or eliminating air leaks, thus resulting in less disruption of sleep.

While aspects of the invention have been illustrated and described, it is not intended that these aspects illustrate and describe all possible forms of the invention. It is understood that the features of various implementing aspects may be combined to form further aspects of the invention. The words used in the specification are words of description rather than limitation, and it is understood that various changes may be made without departing from the spirit and scope of the invention.

What is claimed is:

1. A liner for use with a respiratory mask having a face-engaging portion, the liner comprising:
   a body constructed from an absorbent material, the body having an outer edge, an inner edge, and an opening bounded by the inner edge, wherein a perimeter of the outer edge is larger than a perimeter of the face-engaging portion of the respiratory mask for forming an extending portion of the body, the extending portion configured to be in non-adhering communication with a user's face, and the liner is configured to be releasably held by the mask and the user's face such that the outer edge extends beyond the face-engaging portion.

2. The liner according to claim 1, wherein the extending portion is a baffle for regulating the flow of air away from the face-engaging portion.

3. The liner according to claim 1, wherein the extending portion configured to generally follow the contour of the user's face.

4. The liner according to claim 1, wherein the outer edge has a shape scaled to a general shape of the face-engaging portion.

5. The liner according to claim 1, wherein the body comprises a single layer of material.

6. The liner according to claim 1, wherein the material is stretchable.

7. The liner according to claim 1, wherein the material includes cotton.

8. The liner according to claim 1, wherein the outer edge is spaced apart from the mask when the liner is releasably held by the mask and the user's face.

9. The liner according to claim 1, wherein the liner is configured to be held by pressure of the mask on the user's face without requiring securing of the liner to the mask.

10. The liner according to claim 1, wherein the perimeter of the liner is a continuous perimeter.

11. The liner according to claim 1, wherein the liner is disposable.

12. A liner for use with a respiratory mask having a face-engaging portion, the liner comprising:
    a body having an outer edge, an inner edge, and an opening bounded by the inner edge, wherein a perimeter of the outer edge is larger than a perimeter of the face-engaging portion, the perimeter being discontinuous, and the liner is configured to be releasably held between the mask and a user's face such that a first portion of the body is covered by the face-engaging portion and a second, extending portion of the body extends beyond the mask face-engaging portion with the outer edge spaced apart from the mask, the extending portion configured to be in non-adhering communication with the user's face.

13. The liner according to claim 12, wherein the extending portion is a baffle for regulating the flow of air away from the face-engaging portion.

14. The liner according to claim 12, wherein the extending portion is configured to generally follow the contour of the user's face.

15. A two-piece liner system for use with a respiratory mask having a face-engaging portion and a forehead stabilizer portion, the system comprising:
    a mask liner including a body constructed from an absorbent material, the body having an outer edge, an inner edge, and an opening bounded by the inner edge, wherein a perimeter of the outer edge is larger than a perimeter of the face-engaging portion of the respiratory mask for forming an extending portion of the body, the extending portion configured to be in non-adhering communication with a user's face, and the mask liner is configured to be releasably held by the face-engaging portion and the user's face such that the outer edge extends beyond the face-engaging portion; and
    a forehead liner having a generally rectangular shape with an area at least as large as an area of the forehead stabilizer portion, wherein the forehead liner is configured to be releasably held by the forehead stabilizer portion and the user's face.

16. The system according to claim 15, wherein the forehead liner comprises a multi-layer material.

17. The system according to claim 15, wherein the mask and forehead liners are disposable.

18. The system according to claim 15, wherein the mask liner body comprises a single layer of material.

19. The system according to claim 15, wherein the extending portion is a baffle for regulating the flow of air away from the face-engaging portion.

20. The system according to claim 15, wherein the extending portion is configured to generally follow the contour of the user's face.

* * * * *